United States Patent [19]
Fürst et al.

[11] 3,984,476
[45] Oct. 5, 1976

[54] D-HOMO-19-NORSTEROIDS

[76] Inventors: Andor Fürst, 14 Magnolienpark, Basel; Marcel Müller, 10 Quellenweg, Frenkendorf; Jürg Albert Walter Gutzwiller, 10a Obere Dorfstrasse, Bettingen, all of Switzerland; Ulrich Kerb, 8 Waitzstrasse; Rudolf Wiechert, 5 Petzowerstrasse, both of Berlin, Germany

[22] Filed: Oct. 14, 1975

[21] Appl. No.: 621,850

[30] Foreign Application Priority Data

Oct. 18, 1974 Switzerland............ 13989/74
Sept. 23, 1975 Switzerland............ 12343/75
Oct. 2, 1975 Switzerland............ 12784/75

[52] U.S. Cl. ............ 260/586 E; 260/473 R; 260/475 SC; 260/483; 260/484 R; 260/484 A; 260/485 L; 260/611 F; 260/617.5; 424/308; 424/312; 424/313; 424/331; 424/339; 424/343

[51] Int. Cl.$^2$............ C07C 49/45

[58] Field of Search............ 260/586 E, 483, 484, 260/484 A, 473 R, 611 F, 617.5, 475 SC, 485 L

[56] References Cited
UNITED STATES PATENTS

| | | | |
|---|---|---|---|
| 2,324,881 | 7/1943 | Ruzicka et al. | 260/586 E |
| 2,732,405 | 1/1956 | Dodson et al. | 260/586 E |
| 2,784,234 | 3/1957 | Dodson | 260/568 E |
| 3,194,832 | 7/1965 | Reimar et al. | 260/488 B |
| 3,492,338 | 1/1970 | Hader et al. | 260/488 B |
| 3,555,096 | 1/1971 | Hughes et al. | 260/586 E |

FOREIGN PATENTS OR APPLICATIONS

1,100,441  1/1968  United Kingdom............ 260/586 E

*Primary Examiner*—Gerald A. Schwartz
*Attorney, Agent, or Firm*—Samuel L. Welt; George M. Gould; Raymond R. Wittekind

[57] ABSTRACT

D-Homosteroids of the formula

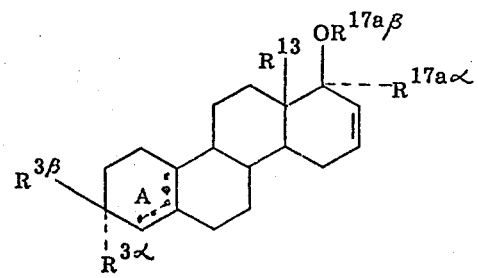

wherein $R^3{}_\alpha$ is hydrogen, $R^3{}_\beta$ is hydrogen, lower alkanoyloxy or aroyloxy and $R^3{}_\alpha$ and $R^3{}_\beta$ taken together are oxo; $R^{13}$ is lower alkyl; $R^{17a}{}_\beta$ is hydrogen, lower alkanoyl, aroyl or lower alkyl; $R^{17a}{}_\alpha$ is hydrogen, lower alkyl, ethynyl, 1-propynyl, vinyl, chloroethynyl, butadiynyl or propadienyl and the dotted line in the A-ring denotes an additional carbon bond in either the 4,5- or 5(10)-position and processes for the preparation thereof are disclosed.

The D-homosteroids of the present invention are useful as contraceptives and regulators of the female menstrual cycle.

10 Claims, No Drawings teroids of formula I wherein $R^{17a\alpha}$ represents a hydrogen atom or an ethynyl, chloroethynyl or butadiynyl group and $R^{17a\beta}$ represents a hydrogen atom.

Examples of D-homosteroids of formula I in which $R^{3\alpha}$ and $R^{3\beta}$ represent hydrogen or $R^{3\alpha}$ represents hydrogen and $R^{3\beta}$ represents lower alkanoyloxy are 17β-hydroxy-13-methyl-gona-4,16-diene;

17aα-ethynyl-17aβ-hydroxy-13-methyl-gona-4,16-diene;

17aα-ethynyl-13-ethyl-17aβ-hydroxy-gona-4,16-diene;

17aβ-acetoxy-17aα-ethynyl-13-ethyl-gona-4,16-diene;

3β-17aβ-diacetoxy-13-methyl-gona-4,16-diene;

3β,17αβ-diacetoxy-17aα-ethynyl-13-methyl-gona-4,16-diene and

3β,17aβ-diacetoxy-17aα-ethynyl-13-ethyl-gona-4,16-diene.

Examples of the residue or grouping $R^{31}$ are 3-alkoxy (e.g., 3-methoxy)$\Delta^{2,5(10)}$-, 3-alkylthio (e.g., 3-methylthio)-$\Delta^{2,5(10)}$-, 3-sec.-amino (e.g., pyrrolidino)-$\Delta^{2,5(10)}$-, 3-alkylenedioxy (e.g., ethylenedioxy)-$\Delta^{5(10)}$-, $\Delta^4$- or $\Delta^5$-, or 3-alkylenedithio (e.g., 3-ethylenedithio)-$\Delta^{5(10)}$-, $\Delta^4$- or $\Delta^5$-groupings.

The hydrolysis according to process variant (a) can be accomplished in a manner known per se with acids, e.g., mineral acids such as hydrochloric acid; or with carboxylic acids such as oxalic acid. Especially suitable reaction media are aqueous-alcoholic solutions such as methanol/water, which may optionally contain an additional solvent such as chloroform.

The reaction of the 17aα-keto group of a compound of formula III with a organometallic compound according to process variant (b) can also be carried out in a manner known per se. The organometallic compound can be a Grignard compound (e.g., ethynylmagnesium bromide, propynylmagnesium bromide, vinylmagnesium bromide) or an alkali organometallic compound, such a sodium, potassium or lithium acetylide, or vinyllithium.

The reduction of a compound of formula III according to embodiment (c) of the present process can be carried out in a manner known per se with complex metal hydrides [e.g. di(lower alkyl)-aluminium hydrides such as diisobutylaluminium hydride; tri(lower alkoxy)-aluminiums such as triisopropoxyaluminium; lithium aluminium hydride, sodium aluminium or sodium (boro) hydride; trimethoxy- or tributoxy-(lithium aluminium hydride)], suitable solvents for this reduction are hydrocarbons such as cyclohexane, benzene and toluene or ethers such as diethyl ether and tetrahydrofuran.

The D-homosteroids of the formulae II and III used as starting materials can be prepared by the methods described in the following section or by analogy thereto.

A. Preparation of
3-methoxy-D-homo-19-nor-17aα-pregna-2,5,(10), 16-trien-20-yn-17a-ol a. A boiling solution of 44 g. of 3-methoxy-D-homoestra-1,3,5(10)-trien-17a-one in 100 ml. of dichloromethane and 200 ml. of methanol was treated with a suspension of 62 g. of copper$^{II}$ bromide in 40 ml. of methanol and 30 ml. of dichloromethane and the reaction mixture was stirred for 5 hours under reflux. The crystalline precipitate was filtered over Speedex under suction, rinsed with dichloromethane and the filtrate was concentrated to dryness on a rotary evaporator. The residue was taken up in dichloromethane, washed 3 times with water and the aqueous phases were extracted a further two times with dichloromethane. The organic phases were dried over sodium sulfate and concentrated on a rotary evaporator. The 17β-bromo-3-methoxy-D-homesestra-1,3,5(10)-trien-17a-one was crystallized from dichloromethane-hexane; m.p. 183°–184°; $[\alpha]_D^{25}$ +32° ($CHCl_3$; c=1.0).

b. A solution of 49 g. of 17β-bromo-3-methoxy-D-homestra-1,3,5(10)-trien-17a-one in 400 ml. of dimethylformamide was treated with 43.5 g. of lithium bromide and with 18.5 g. of lithium carbonate and the mixture stirred at 110° bath temperature for 10 hours under argon. The reaction mixture was poured onto ice-water and extracted 3 times with dichloromethane. The organic extracts were back-washed two times with water, dried over sodium sulfate and concentrated on a rotary evaporator. The last residues of dimethylformamide were removed at 0.5 Torr/70°. Crystallization from dichloromethane-acetone gave 3-methoxy-D-homoestra-1,3,5(10),16-tetraen-17a-one; m.p. 161°–162°; $[\alpha]_D^{25}$ ±0° ($CHCl_3$; c=1.0).

c. A solution of 36.5 g. of 3-methoxy-D-homestra-1,3,5(10),16-tetraen-17a-one in 750 ml. of abs. tetrahydrofuran was treated portionwise with 3.8 g. of lithium aluminum hydride with stirring in an argon atmosphere at 0°–5°. After stirring at 0° for 2 hours, the mixture was treated carefully with ethyl acetate, then with ice-water and filtered over Speedex under suction. The filtrate was extracted 3 times with ethyl acetate, the organic phases washed 2 times with water, dried over sodium sulfate and concentrated to dryness on a rotary evaporator. Crystallization of the crude product from ether-hexane yielded 3-methoxy-D-homestra-1,3,5(10),16-tetraen-17aβ-ol, m.p. 100°–101°; $[\alpha]_D^{25}$ +28° (chloroform; c=1.0).

d. A solution of 33 g. of 3-methoxy-D-homoestra-1,3,5(10),16-tetraen-17-β-ol in 300 ml. of abs. tetrahydrofuran and 300 ml. of tert.-butanol was added dropwise within 15 minutes to 750 ml. of abs. liquid ammonia at −33°. 10.2 G. of sodium were added portionwise to the milky suspension. The dark blue mixture was stirred for 2 hours at −33°, carefully treated with 100 ml. of methanol and freed from ammonia by slowly warming to room temperature. The mixture was poured onto ice-water and extracted with dichloromethane. The organic phases were back-washed two times with water, dried over sodium sulfate and evaporated to dryness on a rotary evaporator. Crystallization from ether-hexane yielded 3-methoxy-D-homoestra-2,5(10),16-trine-17aβ-ol; m.p. 119°–120°; $[\alpha]_D^{25}$ +90° (chloroform; c=1.0).

e. A solution of 16 g. of 3-methoxy-D-homestra-2,5(10),16-trien-17aβ-ol in 200 ml. of benzene was treated with a suspension of 50 g. of silver carbonate on Speedex [M. Fetizon etl., J. Org. Chem. 36, 1341 (1971)] in 400 ml. of benzene, and the mixture was heated to reflux for 3 hours under argon. The black precipitate was filtered off under suction, rinsed with ether, and the filtrate concentrated to dryness on a rotary evaporator. Crystallization from ether-hexane yielded 3-methoxy-D-homoestra-2,5(10),16-trien-17a-one; m.p. 159°–151°; $[\alpha]_D^{25}$ −86° (chloroform; c=0.95).

f. A solution of 3.7 g. of 3-methoxy-D-homestra-2,5(10),16-trien-17a-one in 75 ml. of abs. tetrahydrofuran was treated with 3.4 g. of lithium acetylide-ethylenediamine complex and the mixture was stirred

D-HOMO-19-NORSTEROIDS

Description of the Invention

This invention relates to novel D-Homosteroids of the formula

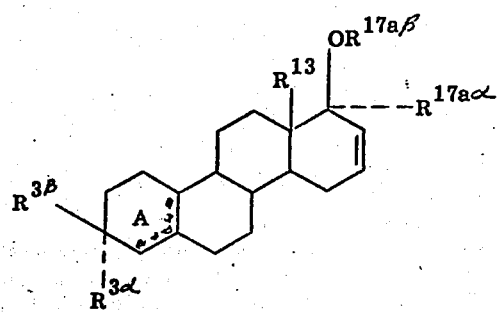

I wherein $R^{3\alpha}$ is hydrogen, $R^{3\beta}$ is hydrogen, lower alkanoyloxy or aroyloxy and $R^{3\alpha}$ and $R^{3\beta}$ taken together are oxo; $R^{13}$ is lower alkyl; $R^{17a\beta}$ is hydrogen, lower alkanoyl, aroyl or lower alkyl; $R^{17a\alpha}$ is hydrogen, lower alkyl, ethynyl, 1-propynyl, vinyl, chloroethynyl, butadinynyl or propadienyl and the dotted line in the A-ring denotes an additional carbon to carbon bond in either the 4,5 or 5(10)-position.

The D-homosteroids of formula I are prepared in accordance with the invention by a. hydrolyzing a D-homosteroid of the formula

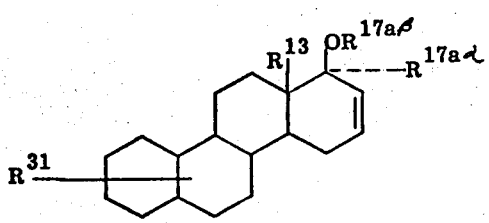

II wherein $R^{13}$, $R^{17a\beta}$ and $R^{17a\alpha}$ are as above; $R^{31}$ is a residue hydrolyzable to form a 3-keto- $\Delta^4$-or 3-keto- $\Delta^{5(10)}$ -grouping, or b. reacting a D-homosteroid of the formula

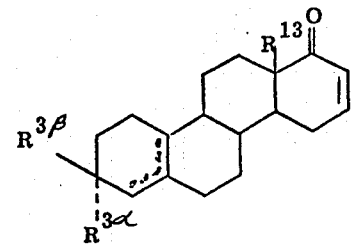

III wherein $R^{13}$ and the dotted line in the A-ring are as above; $R^{3\alpha}$ is hydrogen and $R^{3\beta}$ is hydrogen, lower alkanoyloxy or aroyloxy
with an organometallic compound furnishing the $R^{17a\alpha}$ residue, or c. reducing the keto group in a compound of formula III hereinbefore to a hydroxy group.

As used throughout the specification and appended claims, the term "alkanoyl" denotes the residue obtained by removal of the hydroxyl portion of alkanecarboxylic acids. Examples of alkanoyl groups are acetyl, propionyl, caproyl, valeryl, oxalyl, succinyl and citroyl. The term "aroyl" denotes the residue obtained by removal of the hydroxyl portion of aromatic carboxylic acids. An example of an aroyl group is benzoyl. The term "alkyl" denotes straight-chain or branched-chain hydrocarbon groups. Examples are methyl, ethyl, isopropyl, tertiary-butyl and isomers thereof. As applied to the foregoing and following groups, the term "lower" denotes a group having a carbon skeleton containing 1 to 7 carbon atoms. By the terms "alkanoyloxy" and "aroyloxy" are meant residues formed by removal of the hydroxyl proton from the aforementioned alkanecarboxylic acids and aromatic carboxylic acids, respectively. An example of an alkanoyloxy group is acetoxy, and an example of an arolyoxy group is benzoyloxy.

In the formulas presented herein the various substituents are illustrated as joined to the steroid nucleus by one of two notations: a solid line (—) indicating a substituent which is in the β-orientation (i.e., above the plane of the molecule) and a broken line (---) indicating a substituent which is in the α-orientation (i.e., below the plane of the molecule). The formulas have all been drawn to show the compounds in their absolute stereochemical configuration. Inasmuch as the starting materials, as well as the final products, are derived from naturally occurring materials, they exist in the single absolute configuration depicted herein. The processes of the present invention, however, are intended to apply as well to the synthesis of steroids of the racemic series.

A preferred group of D-homsteroids of formula I are those wherein $R^{3\alpha}$ and $R^{3\beta}$ together represent an oxo grouping, $R^{13}$ represents a methyl or ethyl group and the double bond in ring A is present in the 4,5-position. More especially preferred are such D-homosfor 90 minutes at 25° under argon. The mixture was poured onto ice-water and extracted 3 times with ca. 1:1 ether/ethyl acetate. The organic phases were washed with water, dried over sodium sulfate and evaporated to dryness on a rotary evaporator: 3-methoxy-D-homoestra-2,5(10),16-trien-17a-one; m.p. 139°–140° (hexane); $[\alpha]_D^{25}$ −86° (chloroform; c=0.816).

B. Preparation of 13-ethyl-3-methoxy-D-homo-18,19-dinor-17aα-pregna-2,5(10),16-trien-20-yn-17a-ol a. A boiling solution of 25 g. of 13-ethyl-3-methoxy-D-homogona-1,3,5(10)-trien-17a-one prepared from 13-ethyl-3-methoxygona-1,3,5(10)-trien-17-one by: (1) conversion into the corresponding 17-cyanohydrin, (2) reduction of the cyanohydrin to the corresponding primary amine and N-nitrosation with nitrous acid with simultaneous ring extension [cf. Helv. 24, 295$_E$ (1941)] in 50 ml. of dichloromethane and 100 ml. of methanol was treated with a suspension of 36.2 g. of copper$^{II}$ bromide in 20 ml. of dichloromethane and 20 ml. of methanol and the mixture was stirred for 18 hours under reflux. The crystalline precipitate was filtered over Speedex under suction, thoroughly rinsed with dichloromethane and the filtrate was evaporated to dryness on a rotary evaporator. The residue was taken up in dichloromethane, washed 3 times with water and the aqueous phases were further extracted 2 times with dichloromethane. After drying over sodium sulfate, with concentration on a rotary evaporator the 13-ethyl-17-bromo-3-methoxy-D-homoestra-1,3,5(10)-trien-17a-one crystallized out. Further crystalline α-bromoketone was obtained from the mother liquors after chromatography on 1 kg. of silica gel with 2% ethyl acetate-benzene as the eluant. 28 G. of α-bromoketone were dissolved in 400 ml. of dimethylformamide, treated with 20.4 g. of lithium bromide and 8.3 g. of lithium carbonate and the mixture was stirred at 110° bath temperature for 7 hours under argon. The mixture was poured onto ice-water and extracted 1 time with ether-dichloromethane (2:1) and 2 times with ether. The organic extracts were back-washed 2 times with water, dried over sodium sulfate and evaporated on a rotary evaporator. After chromatography on 700 g. of silica gel with benzene as the eluant and crystallization from dichloromethane-acetone, there was obtained 13-ethyl-3-methoxy-D-homogona-1,3,5(10),16-tetraen-17a-one; m.p. 169°–170°; $[\alpha]_{589}^{25}$ −20° (dioxane; c=0.103).

b. A solution of 12 g. of 13-ethyl-3-methoxy-D-homogona-1,3,5(10),16-tetraen-17a-one in 400 ml. of abs. tetrahydrofuran was treated portionwise with 1.6 g. of lithium aluminum hydride in an argon atmosphere while stirring at 0–5°. After stirring at 0° for 60 minutes, the mixture was treated carefully with ethyl acetae, then with ice-water and filtered over Speedex under suction. The filtrate was extracted three times with ethyl acetate, the organic phases washed 2 times with water, dried over sodium sulfate and evaporated to dryness on a rotary evaporator. After chromatography of the crude product on 1 kg. of silica gel (0.06–0.2 mm) with hexane-ethyl acetate (7:1) as the eluant, there was obtained 13-ethyl-3-methoxy-D-homogona-1,3,5(10),16-tetraen-17aβ-ol; m.p. 138°–139° (ether); $[\alpha]_{589}^{25}$ +18° (dioxane; c=0.099).

c. A solution of 9 g. of 13-ethyl-3-methoxy-D-homogona- 1,3,5(10),16-tetraen-17aβ-ol in 100 ml. of abs. tetrahydrofuran and 100 ml. of tert.-butanol was added dropwise within 20 minutes to 250 ml. of abs. liquid ammonia at −33°. 4.5 G. of sodium were added portionwise to the milky suspension. The dark blue mixture was stirred for 4½ hours at −33°, treated carefully with 50 ml. of methanol and freed from ammonia by slowly warming to room temperature. The mixture was poured onto ice-water and extracted 3 times with dichloromethane. The organic phases were back-washed two times with water, dried over sodium sulfate and evaporated to dryness on a rotary evaporator: 13-ethyl-3-methoxy-D-homogona-2,5(10),16-trien-17aβ-ol; m.p. 166°–170° (CH$_2$Cl$_2$).

d. A solution of 1 g of 13-ethyl-3-methoxy-D-homogona-2,5(10),16-trien-17aβ-ol in 100 ml. of benzene was treated with a suspension of 15 g. of silver carbonate on Speedex in ca. 100 ml. of benzene, and the mixture was heated at reflux under argon for 48 hours. The residue obtained by evaporation of the filtrate yielded, after chromatography on 30 g. of Alox neutral, activity III, with benzene elution, 13-ethyl-3-methoxy-D-homogona-2,5(10),16-trien-17a-one; m.p. 168°–172°.

e. A solution of 0.9 g. of crude 13-ethyl-3-methoxy-D-homogona-2,5(10), 16-trien-17a-one in 20 ml. of abs. tetrahydrofuran was added to a suspension of ethynyl magnesium bromide prepared from 1 g. of magnesium shavings, 4 ml. of ethyl bromide and excess dry acetylene in 30 ml. of tetrahydrofuran. The mixture was stirred under acetylene for 20 hours at 25°, carefully decomposed with ice-water and filtered over Speedex under suction. The filtrate was extracted three times with ether, the organic phases washed with water, dried over magnesium sulfate and evaporated to dryness on a rotary evaporator and yielded 13-ethyl-3-methoxy-D-homo-18,19-dinor-17aα-pregna-2,5(10),16-trien-20-yn-17a-ol, C. Preparation of 13-ethyl-17a-hydroxy-D-homo-18,19-dinor-17aα-pregna-5(10), 16-dien-20-yn-3-one ethylene ketal a. A suspension of 3.1 g. of 13-ethyl-3-methoxy-D-homogona-2,5(10),16-trien-17aβ-ol in 30 ml. of dichloromethane and 25 ml. of ethylene glycol was reduced to ca. 30 ml. volume on a rotary evaporator and treated with 15 ml. of glacial acetic acid. After stirring for 18 hours under argon at 25°, the homogeneous solution was poured onto ice cold aqueous 3N sodium hydroxide and the alkaline phase extracted three times with ether. The organic phases were washed three times with water, dried over magnesium sulfate and concentrated to dryness on a rotary evaporator. After chromatography on 120 g. of silica gel (0.06–0.2 mm) with 5:1 hexane-ethyl acetate as the eluant, there was obtained amorphous 13-ethyl-17aβ-hydroxy-D-homogona-5(10),16-dien-3-one ethylene ketal.

b. A solution of 3.68 g. of 13-ethyl-17aβ-hydroxy-D-homogona-5(10),16-dien-3-one ethylene ketal in 60 ml. of pyridine was treated at 5° with 30 ml. of a 1 molar solution of chromium trioxide in pyridine-water (10:1). After stirring for 18 hours at 25°, the mixture was treated with ice-water and ether, filtered over Speedex under vacuum and the aqueous phase of the filtrate extracted three times with ether. The organic phases were washed 3 times with water, dried over magnesium sulfate and evaporated on a rotary evaporator. After chromatography on 100 g. of silica gel (0.06–0.02 mm) with hexane-ethyl acetate as the eluant, there was obtained 13-ethyl-D-homogona- 5(10),16-diene-3,17a-dione 3-ethylene ketal, m.p. 86°–88° (ether); $[\alpha]_{589}^{25}$ +52° (dioxane; c = 0.105).

c. A solution of 2.6 g. of 13-ethyl-D-homo-5(10),16-diene-3,17a-dione-3-ethylene ketal in 30 ml. of abs. tetrahydrofuran was added to a suspension of ethynylmagnesium bromide prepared from 2 g. of magnesium shavings, 8 ml. of ethyl bromide and excess dry acetylene in 100 ml. of tetrahydrofuran. The mixture was stirred under acetylene at 25° for 20 hours, carefully decomposed with ice-water, covered with ether and converted into a homogeneous two-phase system by the addition of aqueous 3N sulfuric acid. The aqueous phase was extracted three times with ether, the organic extracts washed 1 time with aqueous bicarbonate solution and 1 time with water, dried over magnesium sulfate and evaporated to dryness on a rotary evaporator. There was obtained crude 13-ethyl-17a-hydroxy-D-homo-18,19dinor-17aα-pregna-5(10),16-dien-20-yn-3-one ethylene ketal in the form of a yellow foam.

D. Preparation of 17aβ-hydroxy-D-homooestra-5(10),16-dien-3-one ethyleneketal.

13.3 ml of a ca 0.75-M solution of diisobutylaluminium hydride in toluene were added at 0°C with stirring under argon to a solution of 3.3 g of D-homooestra-5(10),16-diene-3,17a-dione 3-ethyleneketal in 50 ml of benzene. After stirring for 45 minutes at 0°C, the mixture was poured on to ice-water and extracted 3 times with ether. The organic phases were back-washed twice with water, dried over sodium sulphate and concentrated on a rotary evaporator. Crystallisation from ether followed by chromatography of the mother liquor on silica gel yielded respectively 2.85 g. of 0.37 g of 17aβ-hydroxy-D-homooestra-5(10),16-dien-3-one ethyleneketal; melting point 166°–168°c.

E. Preparation of 13-ethyl-17aβ-hydroxy-D-homogona-5(10),16-dien-3-one 3-ethyleneketal.

13.3 ml of a ca 0.75-M solution of diisobutylaluminium hydride in toluene were added at 0°C with stirring under argon to a solution of 3.4 g of 13-ethyl-D-homogona-5(10),16-diene-3,17a-dione 3-ethyleneketal in 50 ml of benzene. After stirring for 60 minutes at 0°C, the mixture was poured on to ice-water and extracted 3 times with ether. The organic phases were washed twice with water, dried over sodium sulphate and concentrated on a rotary evaporator. After chromatography on silica gel, there were obtained 3.2 g of amorphous 13-ethyl-17aβ-hydroxy-D-homogona-5(10),16-dien-3-one-3-ethyleneketal.

The compounds of formula I are potent progestational agents and inhibit ovulation. They are useful, for example, as contraceptives and regulators of the femle menstrual cycle. For these purposes, dosages of about 0.01 to about 0.1 mg/kg are effective. Furthermore, an androgenic activity has been observed, especially in D-homosteroids of formula I wherein $R^{17a\alpha}$ represents hydrogen or lower alkyl.

The compounds of this invention can be used in the form of pharmaceutical preparations which contain them in admixture with a pharmaceutical, organic or inorganic, inert carrier material suitable for enteral or parenteral application, such as, for example, water, gelatin, gum arabic, lactose, starch, magnesium stearate, talc, vegetable oils, polyalkyleneglycols, Vaseline and the like, and can be present in a solid form, e.g., as tablets, dragees, suppositories, capsules; or in liquid form, e.g., as solutions, suspensions or emulsions.

The following examples illustrate the invention.

EXAMPLE 1

A solution of 3.9 g. of crude 3-methoxy-D-homo-19-nor-17aα-pregna-2,5(10),16-trien-20-yn-17a-ol in 90 ml. of methanol and 50 ml. of chloroform was treated with 1.8 g. oxalic acid in 50 ml. of water. After stirring at 25° for 3 hours, the mixture was poured onto an ice-cold aqueous bicarbonate solution, the methanol was removed on a rotary evaporator and the aqueous phase was extracted three times with ether-ethyl acetate (1:1). The organic phases were washed 2 times with water, dried over sodium sulfate and concentrated to dryness on a rotary evaporator. After chromatography on 250 g. of Alox, neutral III, with dichloromethane as the eluant, there was obtained 17a-hydroxy-D-homo-19-nor-17aα-pregna-5(10),16-dien-20-yn-3-one; m.p. 182°–184° (hexane); $[\alpha]_{589}^{25}$ −31° (dioxane; c = 0.100).

EXAMPLE 2

A solution of 3.2 g. of crude 3-methoxy-D-homo-19-nor-17aα-pregna-2,5(10),16-trien-20-yn-17a-ol in 40 ml. of methanol was treated with 1.6 ml. of concentrated hydrochloric acid and with 2 ml. of water and held at 25° for 18 hours. The mixture was poured onto brine, xtracted 3 times with dichloromethane, the organic phases were washed 1 time with bicarbonate, dried over sodium sulfate and concentrated to dryness on a rotary evaporator. After chromatography on 150 g. of Alox, neutral III, with hexane-ethyl acetate (4:1) as the eluant, there was obtained 17a-hydroxy-D-homo-19-nor-17aα-pregna-4,16-dien-20-yn-3-one; m.p. 190°–191°; $[\alpha]_{589}^{25}$ −202° (dioxane; c = 0.102).

EXAMPLE 3

A solution of 3 g. of crude 13-ethyl-17a-hydroxy-D-homo-18,19-dinor-17aα-pregna-5(10),16-dien-20-yn-3-one ethylene ketal in 40 ml. of methanol was treated with 0.5 ml. of concentrated hydrochloric acid and 1 ml. of water. After 2½ hours at 25°, the mixture was neutralized with an aqueous bicarbonate solution, the methanol was removed on a rotary evaporator and the aqueous residue was extracted with dichloromethane. The organic phases were washed with water, dried over sodium sulfate and concentrated to dryness on a rotary evaporator. After chromatography on 100 g. of Alox, neutral II, with dichloromethane as the eluant, there was obtained 13-ethyl-17a-hydroxy-D-homo-18,19-dinor-17aα-pregna-4,16-dien-20-yn-3-one; m.p. 227°–230° (dichloromethane-methanol); $[\alpha]_{589}^{25}$ −197° (dioxane; c = 0.072).

EXAMPLE 4

A solution of 0.9 g. of crude 13-ethyl-3-methoxy-D-homo-18,19-dinor-17aα-pregna-2,5(10),16-trien-20-yn-17a-ol in 20 ml. of methanol was treated with 0.4 ml. of concentrated hydrochloric acid and 1 ml. of water. After 4 hours, the mixture was worked up as in Example 3. There was obtained 13-ethyl-17a-hydroxy-D-homo-18,19-dinor-17aα-pregna-4,16-dien-20-yn-3-one.

EXAMPLE 5

A suspension of 3.2 g of 17aβ-hydroxy-D-homooestra-5(10),16-dien-3-one ethyleneketal in 15 ml of methanol was treated with 4 ml of 1-N and with 0.4 ml of concentrated aqueous hydrochloric acid and the mixture stirred at 0°C for 15 hours, a homogeneous solution resulting. The methanol was evaporated on a rotary evaporator, the residue was treated with ice-water and then extracted 3 times with dichloromethane. After washing with bicarbonate solution, drying over sodium sulphate and concentration on a rotary evaporator, the crude product obtained was adsorbed on 100 g of silica gel (0.06–0.2 mm). Elution with dichloromethane/1% ether yielded 2.5 g of 17a$\beta$-hydroxy-D-homooestra-4,16-dien-3-one; melting point 132°–133°C; $[\alpha]_{589}^{25} = +29°$ (c = 0.100 in dioxane).

EXAMPLE 6

A solution of 3 g of 3-methoxy-D-homooestra-2,5(10),16-trien-17a$\beta$-ol in 150 ml of methanol was treated with 30 ml of 1-N aqueous hydrochloric acid and kept at 25°C for 15 hours. The methanol was evaporated on a rotary evaporator and the aqueous residue extracted 3 times with dichloromethane. The organic phases were washed with bicarbonate solution, dried over sodium sulphate and concentrated on a rotary evaporator. There were obtained 2.8 g of 17a$\beta$-hydroxy-D-homooestra-4,16-dien-3-one; melting point 132°–133°C.

EXAMPLE 7

A solution of 3.14 g of 13-ethyl-3-methoxy-D-hmogona-2,5(10),16-trien-17a$\beta$-ol in 150 ml of methanol was treated with 10 ml of 1-N and with 3 ml of concentrated aqueous hydrochloric acid and stirred at 25°C for 12 hours. The methanol was evaporated on a rotary evaporator and the aqueous residue extracted 3 times with dichloromethane. The organic phases were washed with bicarbonate solution, dried over sodium sulphate and concentrated on a rotary evaporator. There were obtained 2.9 g of 13-ethyl-17a$\beta$-hydroxy-D-homogona-4,16-dien-3-one; melting point 191°–192°C.

EXAMPLE 8

A suspension of 3.2 g of 13-ethyl-17a$\beta$-hydroxy-D-homogona-5(10),16-dien-3-one in 20 ml of methanol was treated with 5 ml of 1-N and 0.3 ml of concentrated aqueous hydrochloric acid and stirred for 2 hours. The homogenous solution was kept at +5°C for 2.5 days, after which 0.93 g of crystalline 13-ethyl-17a$\beta$-hydroxy-D-homogona-4,16-dien-3-one had separated. After the usual working-up of the filtrate and chromatography on silica gel, there were obtained a further 1.0 g of 13-ethyl-17a$\beta$-hydroxy-D-homogona-4,16-dien-3-one; melting point 191°–192°C; $[\alpha]_{589}^{25} = +12°$ (c = 0.101 in dioxane).

EXAMPLE 9

12 ml of a ca 2-M ethereal solution of n-butyllithium were added while stirring under argon at −20°C to a solution of 1.16 g of trans-1,2-dichloroethylene in 20 ml of ether. After stirring at −20°C for 30 minutes a solution of 1 g of D-homooestra-5(10),16-diene-3,17a-dione 3-ethyleneketal in 20 ml of ether was added with stirring and the mixture stirred for 2 hours at 0°C and for 1.5 hours at 25°C. The mixture was poured on to an ice-cold aqueous ammonium chloride solution and extracted three times with ether. The organic phases were washed with water, dried over sodium sulphate and concentrated on a rotary evaporator. The 1.5 g of crude substance obtained were crsytallised from dichloromethane/ether to give 0.48 g of 13-ethyl-21-chloro-17a-hydroxy-D-homo18,19dinor-17a$\alpha$-pregna-5(10),16-dien-20-yn-3-one ethyleneketal, a further 0.47 g of same being obtained after chromatography of the mother liquor on silica gel; melting point 191°–192°C; $[\alpha]_{589}^{25} = -143°$ (c = 0.102 on dioxane).

A solution of 0.5 g of 13ethyl-21-chloro-17a-hydroxy-D-hom0-18,19-dinor-17a$\alpha$-pregna-5(10),16-dien-20-yn-3-one ethyleneketal in 20 ml of methanol was treated with 10 ml of 1-N aqueous hydrochloric acid and stirred at 25°C for 24 hours. After removal of the methanol on a rotary evaporator, the residue was partitioned between ether and aqueous bicarbonate solution, the ethereal phases were washed with water, dried over sodium sulphate and concentrated on a rotary evaporator. Crystallisation from ether/hexane yielded 0.35 g of 13-ethyl-21-chloro-17a-hydroxy-D-homo-18,19-dinor-17a$\alpha$-pregna-4,16-dien-20-yn-3-one; melting point 198°–199°C; $[\alpha]_{589}^{25}$.

EXAMPLE 10

7.5 ml of ca 1.5-M solution of methyllithium were added with stirring under argon at 0°C to a solution of 3.4 g of D-homooester-5(10), 16-dine-3,17a-dione 3-ethyleneketal in 20 ml of tetrahydrofuran. After stirring at 0°C for 1 hour the mixture was pourd on to ice-water and extracted 4 times with ether. The ethereal phases were washed with water, dried over sodium sulphate and evaporated on a rotary evaporator. The 4 g of crude substance obtained were adsorbed on 150 g of silica gel (0.06–0.2 mm) and eluted with dichloromethane to give 2.8 g of amophous 13-ethyl-17a$\beta$-hydroxy-17a-methyl-D-homogona-5(10),16-dien-3-one ethyleneketal.

A solution of 2.5 g of 13-ethyl-17a$\beta$hydroxy-17a-methyl-D-homogona-5(10),16-dien-3-one ethyleneketal in 30 ml of methanol was treated with a solution of 0.25 g of oxalic acid in 10 ml of water and kept at 5°C for 4 days and at 25°C for 24 hours. The mixture was made slightly alkaline with an aqueous ammonia solution, the methanol was removed on a rotary evaporator and the aqueous residue was extracted with dichloromethane. The organic phases were washed with water, dried over sodium sulphate and evaporated on a rotary evaporator. The residue was adsorbed on 150 g of silica gel (0.06–0.2 mm) and eluted with benzene to give 0.12 g of 13-ethyl-17a$\beta$-hydroxy-17a-methyl-D-homogona-4,16-dien-3-one; melting point 159°–160°C; $[\alpha]_{589}^{25} = -54°$ (c = 0.099 in dioxane).

The following Example illustrates a pharmaceutical preparation containing a D-homosteroid of formula I:

EXAMPLE A

A tablet for oral administration of the following composition can be manufactured:

| | |
|---|---|
| 13-Ethyl-17a -hydroxy-D-homo-18,19--dinor-17a$\alpha$-pregna-4,16-dien-20-yn-3-one | 1 mg |
| Lactose | 60 mg |
| Starch | 37 mg |
| Talcum | 1.8 mg |
| Magnesium stearate | 0.2 mg |
| Total weight | 100 mg |

We claim:
1. A compound of the formula

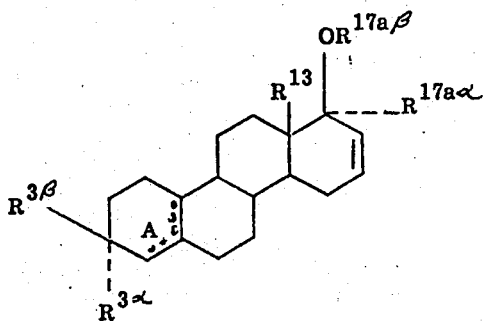

wherein $R^{3\alpha}$ is hydrogen, $R^{3\beta}$ is hydrogen, lower alkanoyloxy or conventional steroid aroyloxy and $R^{3\alpha}$ and $R^{3\beta}$ taken together are oxo; $R^{13}$ is lower alkyl; $R^{17a\beta}$ is hydrogen, lower alkanoyl, conventional steroid aroyl or lower alkyl; $R^{17a\alpha}$ is hydrogen, lower alkyl, ethynyl, 1-propynyl, vinyl, chloroethynyl, butadiynyl or propadienyl and the dotted line in the A-ring denotes an additional carbon to carbon bond in either the 4,5- or 5(10)-position.

2. A compound of claim 1 wherein $R^{3\alpha}$ and $R^{3\beta}$ taken together are oxo; $R^{13}$ is methyl or ethyl; and the double bond in the A-ring is in the 4,5-position.

3. A compound of claim 2 wherein $R^{17a\alpha}$ is hydrogen, ethynyl, chloroethynyl or butadiynyl and $R^{17a\beta}$ is hydrogen.

4. The compound of claim 3 which is 17a-hydroxy-D-homo-19-nor-17aα-pregna-4,16dien-20-yn-3-one.

5. The compound of claim 3 which is 13-ethyl-17a-hydroxy-D-homo-18,19-dinor-17aα-pregna-4,16dien-20-yn-3-one.

6. The compound of claim 3 which is 13-ethyl-21-chloro-17a-hydroxy-D-homo-18,19-dinor-17aα-pregna-4,16-dien-20-yn-3-one.

7. The compound of claim 3 which is 17aβ-hydroxy-D-homoestra-4,16-dien-3-one.

8. The compound of claim 3 which is 13-ethyl-17aβ-hydroxy-D-homogona-4,16-dien-3-one.

9. The compound of claim 1 which is 17a-hydroxy-D-homo-19-nor-17aα-pregna-5(10),16-dien-20-yn-3-one.

10. The compound of claim 1 which is 13-ethyl-17aβ-hydroxy-17a-methyl-D-homogona-4,16-dien-3-one.

* * * * *